United States Patent [19]
Schmerr et al.

[11] Patent Number: 6,150,172
[45] Date of Patent: Nov. 21, 2000

[54] METHOD AND KIT FOR EXTRACTING PRION PROTEIN

[75] Inventors: Mary Jo Schmerr, Woodward, Iowa; Andrew J. Alpert, Ellicott City, Md.

[73] Assignee: The United States of America as represented by the Secretary of Agriculture, Washington, D.C.

[21] Appl. No.: 09/420,850

[22] Filed: Oct. 19, 1999

Related U.S. Application Data

[60] Provisional application No. 60/115,272, Jan. 8, 1999.

[51] Int. Cl.$^7$ ............................... C07K 1/00; A23J 1/00; G01N 33/53
[52] U.S. Cl. ...................... 435/975; 530/412; 530/422; 435/962; 435/7.1
[58] Field of Search ................................ 435/975, 962, 435/7.1; 530/412, 422

[56] References Cited

U.S. PATENT DOCUMENTS

| | | | |
|---|---|---|---|
| 5,808,011 | 9/1998 | Gawryl et al. | 530/416 |
| 5,998,149 | 12/1999 | Hsich et al. | 435/7.1 |
| 6,020,537 | 2/2000 | Prusiner | 530/350 |

OTHER PUBLICATIONS

Safar et al, Protein Science, V.2(12), p2206–16 (Abstract Only) 1993.

Schmerr, Mary Jo, et al., "Purification of the Prion Protein from Sheep Brain Using Hydrophilic Interaction Chromatography", ABRF'98, Program & Abstracts from Genomes to Function–Technical Challenges of the Post Genome Era, Mar. 21–24, 1998, San Diego, Ca.

Schmerr, Mary Jo, et al., "Capillary Isoelectric Focusing of the Scrapie Prion Protein", *Journal of Chromatography A*, 802, 1997, pp. 135–141.

Schmerr, Mary Jo, et al., "A Diagnostic Test for Scrapie Infected Sheep using a Capillary Electrophoresis Immunoassay with Fluorescent Labeled Peptides", *Electrophoresis*, 1998, 19, pp. 409–414.

Schmerr, Mary Jo, et al., "Use of Capillary Electrophories and Fluorescent Labeled Peptides to Detect the Abnormal Prion in the Blood of Animals that are Infected with a Transmissible Spongiform Encephalopathy", *Journal of Chromatography A*, 853, 1999, pp. 207–214.

Bolton, David C., et al., "Molecular Characteristics of the Major Scrapie Prion Protein", *Biochemistry*, 1984, 23, pp. 5898–5899.

*Primary Examiner*—Louise N. Leary
*Attorney, Agent, or Firm*—M. Howard Silverstein; Curtis P. Ribando; John D. Fado

[57] ABSTRACT

A method for extracting prion protein from a biological material, e.g., an animal tissue or product. In a specific example, abnormal prion protein is extracted from homogenized sheep brain with hexafluoro-2-propanol. The hexafluoro-2-propanol is separated from the aqueous brain preparation by increasing the ionic strength of the aqueous solution. Prion protein in the organic extract can be further purified, or the extract can be tested, e.g., by immunoassay, for the presence of prion protein, and more particularly abnormal prion protein. The extraction process permits testing for the presence of abnormal prior protein, e.g., for diagnosis of transmissible spongiform encephalopathies (TSE).

26 Claims, 2 Drawing Sheets

FIG. 1

FIG. 2

METHOD AND KIT FOR EXTRACTING PRION PROTEIN

BACKGROUND OF THE INVENTION

This application claims benefit to U.S. provisional application 60/115,272 filed Jan. 8, 1999.

FIELD OF THE INVENTION

The present invention relates to a method for extracting prion protein from a biological material, such as, for example, an animal tissue or a biological fluid. The extraction process permits testing for the presence of abnormal prion protein, e.g., for diagnosis of transmissible spongiform encephalopathies.

BACKGROUND OF THE INVENTION

Prion diseases or transmissible spongiform encephalopathies (TSES) cause progressive degenerative disorders of the central nervous system resulting in death (Prusiner, Med. Res. Rev. 16:487, 1996; Weissman, FEBS Letters 289:3, 1996). Scrapie, a TSE in sheep, was first described over 200 years ago (Pattison, Vet. Rec. 123:661, 1988), and is the prototype of these diseases. There are no known treatments for these diseases and no known antemortem tests for the presence of the disease in an animal. Prion diseases are caused by a conformational change of the normal host prion protein to an abnormal structure that forms aggregates. Because of the recent outbreak of bovine spongiform encephalopathy in the United Kingdom and the connection between this TSE and the new variant, Creutzfeld-Jakob (Bruce et al., Nature 389:498, 1997), a human TSE, there is a need for new methods that are both sensitive and accurate to diagnose TSEs. Ideally, this diagnosis could be used to test animals before they show clinical signs and before they enter the human food chain or into pharmaceuticals prepared for human use.

DESCRIPTION OF THE PRIOR ART

Most of the methods used to prepare and purify the disease-causing agents of TSEs involve a complex sequence of enzyme and detergent treatments and centrifugations (Bolton et al., J. Virol. 53:596, 1985). Abnormal prion protein is poorly soluble in the typical biological buffers. One method for obtaining purified abnormal prion protein is hydrophilic interaction chromatography (HILIC) (Alpert, J., Chromatogr. 499:177, 1990), which is the inverse of reversed-phase chromatography. Typically, one starts with 70–85% organic solvent and runs a decreasing organic gradient. Elution is in the order of least to most polar. The mostly organic mobile phases of HILIC are compatible with proteins not normally occurring free in aqueous solution, such as membrane proteins (Jenö et al., Anal. Biochem. 215:292, 1993), β-amyloid peptide (1–43) (Alpert et al., Eighth Symposium of the Protein Society, July 1994, San Diego, Calif.), and histones (Lindner et al., J. Chromatogr. A. 782:55, 1997). Surfactants and other denaturants elute in or near the void volume, while proteins and peptides are generally well-retained.

After HILIC purification, the prion protein can be detected using capillary electrophoresis immunoassay (Schmerr and Jenny, Electrophoresis 19:409, 1998) or by capillary isoelectric focusing (Schmerr et al., J. Chromatogr. A. 802:135, 1998).

As noted above, present analytical methods to detect abnormal prion protein generally are used post mortem, thus there is a need for an antemortem assay for abnormal prion protein. In addition, a method is required for isolation of abnormal prion protein without ultracentrifugation steps, which require instrumentation that is not readily available to veterinary diagnostic laboratories. Centrifugation requires the presence of abnormal prion protein as aggregates, whose large size facilitates pellet formation in the centrifuge tubes. Such aggregates are difficult to dissolve and detect in subsequent steps. The use of centrifugation also jeopardizes the possibility of detecting monomeric abnormal prion protein, potentially decreasing the sensitivity of any assay. There is an even more pressing need for a fast, reliable field assay, such as a qualitative immunoassay, to test livestock for infection with a TSE. Thus, there is a need in the art for an efficient, simple method for extracting abnormal prion protein.

Additionally, the antibodies that have been produced detect abnormal prion protein in its monomeric form, with the exception of the antibody produced to the native abnormal prion protein (Korth et al., Nature 390:74, 1997). As a result, abnormal prion protein must be deaggregated with strong detergents or denaturants; these denaturants must then be removed before performing most immunoassays. Thus, there is a need in the art for a rapid, simple method to extract prion protein free of detergents or denaturants for immunoassay analysis.

The present invention provides a new method for the extraction of all sizes of the abnormal prion protein, whether in aggregated or monomeric form. The invention makes it possible to test for abnormal prion protein in samples from a live animal, e.g., using immunoassays. For example, diagnosis can be based on blood samples, which will allow for the testing of live animals and facilitate the removal of infected animals from flocks and herds, and prevent possible contamination of products for consumption.

SUMMARY OF THE INVENTION

The invention provides a method for extracting abnormal prion protein from a biological material suspected of containing abnormal prion protein. The method comprises incubating a mixture of extraction solvent and an isotonic or hypotonic aqueous preparation of the biological material under conditions effective to extract abnormal prion protein from the biological material into the extraction solvent. The extraction solvent is a polar organic solvent in which the abnormal prion protein is soluble, and it is miscible with a hypotonic or isotonic aqueous solution but immiscible with a lyotropic aqueous solution. Lyotropic activity of the mixture is increased so that the extraction solvent separates as a distinct phase from the aqueous preparation of the biological material to yield extraction solvent containing any abnormal prion protein from the biological material.

The invention further provides a method for detecting the presence of abnormal prion protein in an animal, comprising assaying a separated extraction solvent prepared as described above for abnormal prion protein.

Also provided is a kit for isolating abnormal prion protein from a biological sample. The kit comprises an extraction solvent, which has the characteristics set forth above, and a lyotropic salt or aqueous lyotropic salt solution to add to an aqueous preparation of a biological sample so that the organic solvent becomes immiscible with the aqueous preparation. In another embodiment of the invention, the kit includes a prion protein detection assay, preferably an assay for an abnormal prion protein.

Thus, it is an object of the invention to provide a rapid method for isolating abnormal prion protein from a biological sample.

It is also an object of the invention to provide an early detection method for organisms infected with abnormal prion protein.

It is a further object of the invention to provide a solvent extraction technique for isolating abnormal prion protein from a biological sample.

Still another object of the invention is to simplify analytical testing of a biological material from an animal or human for the presence of abnormal prion protein.

Yet another object of the invention is to provide an extract containing abnormal prion protein for further testing or purification.

These and other objects of the invention are presented in greater detail in the accompanying Drawings and Detailed Description of the Invention.

BRIEF DESCRIPTION OF THE DRAWINGS

FIG. 1. Chromatogram from HILIC of $^{125}$I-prion protein, as detected by radioactivity (open circles) and by absorbance at 280 nm (solid line).

FIG. 2. Antibody binding of HILIC factions of $^{125}$I-prion protein.

DETAILED DESCRIPTION OF THE INVENTION

The present invention provides a method for extracting abnormal prion protein from biological material. The extracted product can be tested by an immunoassay for the abnormal prion protein. This extraction of abnormal prion protein, in conjunction with an immunoassay, can be used to diagnose living organisms for infection with a TSE, and will be of worldwide use for testing for TSE infected animals and humans. Thus, the present invention advantageously permits testing for prion protein in clinics and veterinary labs that lack expensive centrifuges, and further permits testing in the field.

An aqueous preparation of the biological material is combined with an extraction solvent to form a mixture. The extraction solvent is a polar organic solvent in which abnormal prion protein is soluble, and miscible with a non-lyotropic isotonic aqueous solution but immiscible with a lyotropic aqueous solution. In a specific preferred embodiment, the extraction solvent is hexafluoro-2-propanol (also termed hexafluoroisopropanol or HFIP). Although in the examples, infra, the volumes of extraction buffer and aqueous preparation of biological material are about equal, any ratio can be used that yields two distinct phases, as described below.

In a preferred embodiment, the mixture is incubated at a temperature ranging from about 20° C. to about 100° C. Nevertheless, any temperature at which both the extraction solvent and aqueous preparation of biological material are in a liquid phase, i.e., between the freezing point and the boiling point, can be used.

The extraction solvent-biological material mixture is incubated under conditions effective to extract abnormal prion protein from the biological material into the extraction solvent. After incubation, the lyotropic activity of the mixture is increased so that the extraction solvent separates from the aqueous preparation. The extraction solvent containing prion protein is removed from the aqueous preparation of biological material.

According to the invention, the lyotropic activity of the extraction solvent-aqueous preparation can be increased by adding a lyotropic salt. The salt can be added as a solid directly to the mixture, or as a concentrated aqueous solution. Preferred examples of lyotropic salts include sodium sulfate and ammonium sulfate. In a specific embodiment, exemplified infra, the ionic strength is increased by adding about a 1:1 ratio (vol/vol) of 0.5 M sodium sulfate to the mixture.

The invention is particularly advantageous because it does not require obtaining material from autopsy or necropsy. According to the invention, the biological material can be a sample from a living animal. The method of the invention provides for extraction of abnormal prion protein from a biological fluid or organ biopsy for analytical testing. Alternatively, the biological material can be obtained from an autopsy or necropsy, e.g., of animal products to be used for food, pharmaceutical, cosmetic, or other products for use by humans or with other animals. In a further embodiment, the method of the invention can be used to remove prion protein from such materials to ensure that infectious prions are not transmitted.

The extraction method of the invention can be used to extract both normal prion protein and abnormal prion protein. By pretreating the biological sample with proteinase-K, the normal prion protein can be digested. Thus, where only abnormal prion protein is desired, the aqueous preparation of biological material can be pretreated with proteinase-K prior to mixing it with the extraction solvent.

The extraction solution containing any prion protein can be dried to yield an extractant pellet. Prion protein in the solution or extractant pellet can be further purified, e.g., by hydrophilic interaction chromatography.

Abnormal prion protein in an animal can be detected by assaying material in the separated extractant pellet for its presence. Preferably, the assay method is an immunoassay for abnormal prion protein. The sample can be treated with proteinase-K prior to isolation of the prion protein so that no normal prion protein is isolated.

In another aspect, the invention provides kits for isolating abnormal prion protein from a biological sample. In one embodiment, a kit comprises extraction solvent, e.g., hexafluoro-2-propanol. The kit further comprises a lyotropic salt or aqueous lyotropic salt solution to add to an aqueous preparation of a biological sample so that the extraction solvent becomes immiscible with the aqueous preparation.

The invention further provides a kit for detecting the presence of abnormal prion protein from a biological sample. In addition to the kit components described above, the detection kit includes a detection assay for abnormal prion protein. The preferred detection assay for the presence of abnormal prion protein is an immunoassay.

Although this extraction method and kit have been developed primarily for the diagnosis of scrapie (TSE in sheep), they are useful for diagnosis of other TSEs in other vertebrates, particularly in mammalian animals and avians, such as humans, bovines, swine, elk, deer, poultry, and rodents. Abnormal prion protein can be detected in tissue of animals and humans as early as two weeks after infection. A significant application of the process of this invention is detection of abnormal prion protein in human blood. This technique can also be used for extraction of the abnormal prion protein from process material used to produce human pharmaceuticals or other products intended for human use, including food supplements.

As used herein, the term "about" or "approximately" means within 20%, preferably within 10%, and more preferably within 5% of a given value or range.

Biological Materials The present invention permits the extraction of prion protein from a biological material. Generally, prion proteins are found in vertebrates, as discussed above. Therefore, under most circumstances, the biological material will be from an animal or human. Prion protein can also be produced during fermentation processes with eukaryotic cells. It may be expressed as a recombinant prion protein. Of greater concern is the possibility of incidental expression of endogenous prion protein by cells that have been recombinantly modified to express another protein. This possibility is more likely if the cells are of neural origin, such as PC12 cells. In this case, the biological material may be a fermentation product, e.g., recombinant protein.

Examples of biological materials from animals include, but are by no means limited to, tissues, such as brain, muscle (including heart), liver, appendix, pancreas, gastrointestinal tract organs, skin, and lymphoid tissue, such as thymus, spleen, tonsil, lymph nodes, etc. Alternatively, the biological material may be a biological fluid. The term biological fluid refers to cerebrospinal fluid, blood, serum, plasma, milk, urine, saliva, tears, mucous secretions, sweat, semen and bodily fluids comprising these components. It also refers to culture fluid (or culture medium) used in the production of recombinant proteins or containing cells in suspension prior to transplantation. Also encompassed by the term "biological materials" are products made from animal organs or tissues, including serum proteins (such as albumin and immunoglobulin), hormones, food and processed food products, nutritional supplements, bone meal, animal feed, extracellular matrix proteins, gelatin, and other animal by-products used in manufacturing or final goods.

Where the biological material is a solid tissue or product, it must first be dissolved or suspended in an aqueous solution so that it will be suitable for the extraction process. For example, brain tissue may be suspended in sucrose solution (e.g., 0.32 M sucrose) at 10% weight to volume. Other hypotonic or isotonic solutions include 5% dextrose, phosphate buffered saline, tri-buffered saline, HEPES-buffered saline, or any of the foregoing buffers. The biological material in the aqueous solution can also be homogenized, ground, or otherwise disrupted to maximize contact between the extraction solvent and the biological material. However, if a biological fluid is the biological material, addition of liquid is not likely to be necessary, unless to dilute the ionic strength of the biological fluid to permit miscibility of the extraction solvent.

Prion Protein

The term "prion protein" as used herein refers to a native protein expressed in neural tissue, particularly the brain and at lower levels in lymphoid tissues and all other tissues. Under some circumstances, prion protein adopts a pathogenic conformation, which is termed herein abnormal prion protein. Certain mutations of the prion gene in some individuals appear to predispose prion protein to adopt the pathogenic conformation. Exposure of an organism to a transmissible infectious agent, the prion, can also induce the conformational change leading to the pathology.

Abnormal prion protein is much less susceptible to proteolysis than normal prion protein. Treatment of a biological material with a proteinase, particularly proteinase-K, digests normal prion protein, but not abnormal prion protein.

In specific examples, infra, sheep abnormal prion protein ($PrP^{SC}$) is extracted by the method of the invention. However, other prion proteins from other species, particularly those mentioned above, can also be extracted using the method of the invention.

Included in the category of abnormal prion protein are human prion proteins found in the neurodegenerative diseases Kuru, Creutzfeld-Jakob Disease (CJD), Gerstmann-Straussler Syndrome (GSS), and fatal familial insomnia. Some case of CJD and GSS are associated with known mutations of the prion gene. CJD is also associated with exposure to TSEs. For example, as noted above, CJD has been associated with bovine spongiform encephalopathy. The present invention permits, for the first time, extraction of abnormal prion protein in patients prior to autopsy. Detection of extracted abnormal prion protein can be used in the diagnosis of any of these diseases.

Scrapie (sheep, goats) and bovine spongiform encephalopathy (cows) are abnormal prion diseases of animals. Prion proteins have also been isolated in chicken, mink, pigs, mouse, hamster, and guinea pig. Furthermore, mouse, hamster, and guinea pig can develop a spongiform encephalopathy by exposure to prions from human or other animal sources. Prion protein from any of these sources can be detected or extracted by the method of the invention.

Extraction Solvent and Conditions

An extraction solvent for use in the present invention must be capable of separating as a distinct phase from water or an aqueous solution under lyotropic conditions. At the same time, prion protein must be soluble in the extraction solvent. Some polar organic solvents meet these criteria. The preferred polar organic solvent is hexafluoro-2-propanol. Other solvents that can be used include isopropanol; 1,1,1-trifluoro-2-propanol (TFIP); 2,2,3,3-tetrafluoro-1-propanol (tetF1P); perfluoro-t-butyl alcohol (PFtBA); 1,1,1,3,3,3-hexafluoroacetone (HFA); trifluoroacetic acid (TFA); 2,2,2-trifluoro-1-ethanol (TFE); 2,2,3,3,4,4,4-heptafluoro-2-propanol (HFB); 1,1,1,3,3,4,4,4-octafluoro-2-butanol (OFIB); 1-methyl-2-pyrrolidinone (NMP); see Wille et al., J. Mol. Biol., 259:608, 1996. Other possible solvents that can be evaluated include DMSO; tetrahydrofuran; and the like. Alternatively, a solvent that is not miscible with water, but in which prion protein is soluble, could be used.

In a specific embodiment, the solvent is miscible with water, e.g., at physiological ionic strength (isotonic aqueous solution) or lower than physiological ionic strength (hypotonic aqueous solution). However, when the buffer comprises lyotropic salts present at a concentration (or ionic strength) above a threshold value, the extraction solvent is not soluble in the aqueous solution: the two phases separate into an extraction solvent layer and an aqueous solution layer. These are referred to herein as "lyotropic conditions". The value for ionic strength of a lyotropic salt of the aqueous solution which achieves lyotropic conditions can vary depending on the extraction solvent selected and the salt(s) used. It can be readily determined by titration or other systematic variation of lyotropic salt concentration, with testing for miscibility or immiscibility of the extraction solvent with the aqueous solution. As used herein, an aqueous solution with an ionic strength of a lyotropic salt at which the extraction solvent separates from water is referred to as a lyotropic aqueous solution. Aqueous solutions containing lower concentrations of lyotropic salts or physiological salts, such as isotonic buffers, are considered non-lyotropic solutions.

Generally, about equal volumes of an extraction solvent and the aqueous preparation of a biological material are used in a solvent extraction process. However, the ratio of extraction solvent to aqueous preparation can range from about 5:1 to about 1:5, preferably from about 3:1 to about 1:3.

After mixing the extraction solvent with the aqueous preparation, the mixture can be incubated for some period of time and at a particular temperature to enhance extraction of prion protein into the extraction buffer. The incubation time can vary from 1 minute to hours, and can be determined by analyzing the extracted material for the presence of prion protein. After the amount of prion protein in the extraction material versus time reaches a plateau, which can be tested using chromatographic or immunoassay techniques, or both, as described in the Examples, additional incubation will have no effect on the prion protein yield. In a specific embodiment, the incubation time is 5 minutes.

In addition, the temperature of incubation can be adjusted to increase the efficiency of extraction, provided that the extraction solvent and aqueous solution are both liquids at the selected temperature. Warmer temperatures, i.e., above room temperature, are preferred, since they increase the solubility of prion protein in the extraction solvent. Particularly useful are temperatures within the range of about 50° C.–60° C. As with other variables, such as the ionic strength of the aqueous preparation and time of incubation, an optimal temperature can be determined by routine experimentation and testing.

Phase Separation

Various lyotropic salts can be used to increase the ionic strength of the aqueous solution, thereby inducing phase separation. Among the preferred salts are sodium sulfate and ammonium sulfate, which are lyotropic. Both are used at a concentration well below that which precipitates proteins. For example, in a specific embodiment, a 0.5 M solution of sodium sulfate is added to an equal volume of the extraction solvent/aqueous preparation mixture, resulting in a final concentration of 0.25 M sodium sulfate. This concentration is sufficient to induce phase separation of HFIP and water. Other salts can also be used, provided they achieve the requisite lyotropic activity at a concentration at which they are soluble. The term "lyotropic activity" is used herein to refer to the structure-forming properties of a lyotropic salt solution. The lyotropic activity is achieved by achieving a sufficient concentration of lyotropic salt to induce phase separation of the organic and aqueous phases. Protein precipitating concentrations of the lyotropic salt are avoided.

"Lyotropic" or "structure-forming" salts, also known as kosmotropes, promote the ordering of the aqueous solution, thereby excluding organic solutes. If the organic solute is the extraction solvent, phase separation occurs. If it is a protein, the protein is salted out of solution. Good structure-forming salts include sodium or ammonium sulfate, phosphates, citrates, etc. (Washabaugh and Collins, J. Biol. Chem., 261:12477, 1986). (Structure-breaking salts, or chaotropes, include guanidinium hydrochloride, sodium perchlorate, sodium bromide, etc. These have the opposite effect; they drive organic solutes into aqueous solution.) The ionic strength of an aqueous solution is a function of the total number of ions in solution, regardless of whether they are structure-forming or structure-breaking ions. The term "ionic strength" relates to the concentration of a salt.

As discussed above, the lyotropic salt can be added as a solid or concentrated liquid, provided that the final lyotropic salt concentration is effective to induce the phase separation. Preferably, the final ratio of extraction solvent to aqueous phase (which includes the aqueous preparation of biological material and any salt solution) after increasing the lyotropic activity of the mixture is about 1:10 to about 10:1, preferably (and as exemplified infra) about 1:3 to about 3:1, provided that at the lower ratio of extraction solvent to aqueous phase, the final salt concentration is still high enough to induce phase separation.

After increasing the lyotropic activity, the extraction solvent, which now contains any prion protein that was present in the biological material, separates from the aqueous preparation. The separation process takes a few minutes, and is complete when both phases are clear and discrete separation is observed between them. Once the two phases are completely separated, the extraction solvent, now containing any prion protein, can be removed or withdrawn, e.g., by drawing off with a pipette or syringe, or with a separation flask.

The extraction solvent containing any prion protein (termed herein "extract") can be dried, e.g., by evaporation, by lyophilization, or vacuum centrifugation to yield highly concentrated or dry extract. The extract may contain other components, including cellular lipids, lipid membrane-binding proteins, and other more hydrophobic cellular components. If desired, prion protein can be isolated or purified away from these components, e.g., by hydrophilic interaction chromatography, as exemplified infra, or other chromatographic techniques (cation exchange chromagraphy, gel permeation chromatography, reverse-phase chromatography, and affinity chromatography, e.g., on an antibody column).

Alternatively, the concentrated or dried extractant material can be analyzed directly, as described infra, to detect abnormal prion protein.

Prion Protein Detector; Immunoassays

Various prion protein detection assays, including assays for selectively detecting abnormal prion protein, are known in the art to be an effective tool for analyzing prion protein. Capillary gel electrophoresis has proven to be an effective analytical tool for abnormal prion protein (Schmerr and Jenny, Electrophoresis, 19:409, 1998). A preferred method is immunoassay, e.g., as described in Schmerr and Jenny, supra. Antiserum described in this reference is specific for abnormal prion protein, as it was found to react in Western blotting with scrapie-infected brain, but not normal brain. Other antisera reactive with prion protein are well known in the art. A preferred immunoassay is a plate ELISA (for example, Grathwohl et al., J. Virol. Methods, 64:205, 1997).

Thus, in some cases, detection of the presence of prion protein, and particularly abnormal prion protein, is based on the biophysical and chemical characteristics of prion protein. These include proteinase resistance (particularly to proteinase K) and digestion profile (whether with proteolytic enzymes, glucolytic enzymes, chemicals, heat, denaturants, etc.). The effects of such treatments on apparent molecular weight and isoelectric point, and various binding assays, can be evaluated. Proteinase resistance and digestion profile can be detected by chromatography, gel electrophoresis, and other molecular weight-sensitive techniques. Isoelectric point can be measured using capillary isoelectric focusing (IEF) or gel isoelectric focusing, although capillary IEF is able to measure the prion pI of 3 more effectively than most gels. Furthermore, qualitative determination of overall charge (acidity or basicity) can be determined by ion exchange chromatography. Other biophysical techniques known in the art can also be used to identify prion protein.

Examples of assays for detection of prion protein include apparent molecular weight and isoelectric point of the protein, including after heating, cyanogen bromide cleavage, neuraminidase treatment, etc. (Bolton et al., J. Virol., 53:596, 1985); glycosidase treatment and lectin binding (Somerville and Ritchie, J. Gen. Virol., 71:883, 1990); proteinase-K resistance (Race et al., Am. J. Vet. Res., 53:883, 1992); and immunoassay (Farquhar et al., J. Virol. Methods, 24:215, 1989).

Alternatively, sequencing or microsequencing of the extracted, and preferably purified, prion protein permits one to unambiguously confirm its identity.

Immunoassays for prion protein can be accomplished by techniques known in the art, e.g., radioimmunoassay, ELISA (enzyme-linked immunosorbant assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A and protein G assays, immunoelectrophoresis assays, measuring levels thereof in appropriate physiological samples, etc. In one embodiment, antibody binding is detected by detecting a label on the primary antibody. In another embodiment, the primary antibody is detected by detecting binding of a secondary antibody or reagent to the primary antibody.

The extraction method of the invention provides an inexpensive source of prion protein, which can be used to generate additional antibodies. Moreover, because the extraction conditions of the invention differ greatly from conventional extraction conditions, prion protein extracted in accordance with the invention may have a different conformation and elicit a different population of antibodies if used for immunization.

This method shortens the extraction time to 1 to 2 hours. Moreover, because of its simplicity, it can be automated. The method extracts prion protein of all molecular sizes, so it is not limited. It also solubilizes the abnormal prion protein so that most immunoassays can be used to detect it. Furthermore, and not insignificantly, it reduces the infectivity of the abnormal prion protein, making the process safer.

Kits

The components for practicing the present invention can be conveniently provided in a kit form. In its simplest embodiment, a kit of the invention provides extraction solvent, preferably HFIP, and lyotropic salt (or a concentrated lyotropic salt solution) for increasing the lyotropic activity of the extraction solvent-aqueous preparation mixture. The amounts of each component can be pre-measured to provide a specified number of assays. In a further embodiment, the kit will include a sample container, preferably of plastic or a material treated to avoid non-specific binding of prion protein.

As used herein, the term container has its broadest meaning, i.e., any receptacle for holding material or reagent. It can be fabricated from glass, plastic, ceramic, metal, or any other material typically employed to hold reagents. However, an acceptable material will not be reactive with the contents it is intended to hold.

The kit can also include proteinase-K for digesting normal prion protein in the biological sample.

In a further embodiment, the kit includes a sample container with a volume indicator for the aqueous preparation of the biological sample. In this embodiment, the polar organic solvent and the lyotropic salt are optimally provided in pre-measured units for use in conjunction with the sample container. The biological sample preparation can be placed in the sample container. The pre-measured unit of extraction solvent can be added, followed by mixing. Then, the pre-measured unit of lyotropic salt can be added to induce phase separation of the extraction solvent and the water. In still a further embodiment, proteinase-K for treating the aqueous preparation of the biological sample is provided in the kit, preferably in a pre-measured unit.

A kit for extracting prion protein from a tissue sample may include a dilution buffer, such as a 0.32 M sucrose solution or phosphate buffered saline, for homogenization of the tissue for the aqueous preparation of the biological material.

In a further embodiment, in which the kit is a kit for detecting the presence of abnormal prion protein in a biological material or sample, the kit provides an abnormal prion protein detector or assay, as described above. Immunoassays, as described above, are preferred for detection of abnormal prion protein extracted in accordance with the invention.

In still a further embodiment, the kit includes an immunochromatographic membrane or support. The extraction solvent containing any prion protein can be applied to the support directly, or the dried extract can be applied, e.g., after resolubilization. Under appropriate conditions, prion protein can flow through the support. It may be captured, e.g., by immobilized anti-prion antibody, and immobilized prion protein detected. Numerous methods and devices known in the art for immunochromatographic assays can be employed in the invention. Immunochromatographic assays are particularly useful under field conditions, where laboratory equipment is not available. Examples of such assays are provided in U.S. Pat. Nos. 5,248,619, 5,451,504, 5,500,375, 5,624,809, and 5,658,801.

A kit of the invention preferably includes packaging and instructions for its use, e.g., on the packaging or package insert.

The present invention may be better understood by reference to the following non-limiting Examples, which are provided as exemplary of the invention.

EXAMPLE 1

Analysis of Abnormal Prion Protein Extracted From Infected Sheep Brain and Lymph Nodes.

Brain or lymph node tissue from each of two scrapie infected sheep was homogenized in 10% sarcosyl and treated with proteinase K to digest the normal host prion protein but not the altered abnormal form of prion protein. Equal volumes (0.5 mM) of homogenate and HFIP were mixed and incubated for five minutes at 56° C. To this mixture, 0.5 mM of 0.5 M $Na_2SO_4$ were added, and the mixture was incubated an additional five minutes. Under these conditions, the HFIP layer separated from the aqueous layer. The HFIP layer was drawn off and dried in a centrifuge. The dried samples were resuspended in 25 µl of distilled water and mixed. Ten µl of the sample was mixed with 5 µl of 20% SDS buffer and boiled for five minutes at 100° C.

Western blot analysis was performed on a 10% to 15% gradient polyacrylamide gel. The protein was transferred from the polyacrylamide gel to nitrocellulose under standard conditions. The nitrocellulose was blocked by incubation with a solution of 5% fish gelatin, and washed with a Tris-Tween buffer. The nitrocellulose was incubated overnight with a rabbit anti-prion protein (antibody raised against whole prion protein diluted 1 to 2,500; Kascak et al., Immunol. Invest., 26:259, 1997; see also, Miller et al., J. Vet. Diagn. Invest. 5:309; Kascak et al., J. Virol., 59:676, 1986). After incubating with the anti-prion antibody, the nitrocellulose was washed with Tris-Tween and then reacted with an anti-rabbit IgG-HRP (horseradish peroxidase) conjugate and incubated for one hour. The nitrocellulose was then washed extensively and developed with a chemiluminescent reagent (Pierce UltraSuperSignal®). Peroxidase activity was detected using a chemiluminescent imager (Chemi-Imager-4000; Alpha, Innotech).

Extracts from both scrapie infected sheep containing 2.75 µl of material produced bands indicative of abnormal prion protein for both brain tissue and lymph node tissue. A brain tissue extract containing 1.5 µl of material from one of the scrapie infected sheep also produced a band indicative of abnormal prion protein. A Western blot of similar extracts from normal (noninfected) sheep did not produce any bands indicative of abnormal prion protein.

EXAMPLE 2

Analysis of Abnormal Prion Protein Extracted and Purified From Infected Sheep Brain and Lymph Nodes.

This example shows further purification and analysis of abnormal (scrapie) prion protein (PrPsc) using hydrophilic interaction chromatography (HILIC). Tissue samples including sheep brain and lymph nodes were processed with detergent and proteinase K as previously described. The resulting extracts were applied to a HILIC column and eluted with a decreasing gradient of acetonitrile in 0.1% trifluoroacetic acid and 50 mM hexafluoro-2-propanol. Recovery from the column was approximately 75% as determined with a radioiodinated prion protein. After drying, the collected peak fractions were resuspended in water and assayed with antibodies specific for the prion protein. The method permitted efficient purification of the prion protein as well as testing by immunoassay, since interfering detergents were removed.

EXAMPLE 3

Analysis of Abnormal Prion Protein Extracted From Infected Sheep Brain.

Preparation of Sheep Brain Material.

Scrapie infected sheep brains were obtained from field cases that were positive for the abnormal prion by Western blot (Race et al., Am. J. Vet. Res. 53:883, 1992). A pool was made of 3 positive brains. The same pool was used for all the experiments presented here. Normal brains came from sheep from a scrapie-free flock and were negative for abnormal prion protein by Western blot. The brain material was prepared for chromatography by a modification of the method of Bolton et al. (J. Virol. 53:596, 1985). Briefly, the brain stems were dissected out, weighed and placed in 0.32 M sucrose (10% w/v). The material was then homogenized for 60 s with a Brinkman Polytron (Kinematica AG, Lucerne Switzerland) using a 0.7 cm stainless steel generator at the highest speed. The homogenate was centrifuged at 10,000 g for 20 min to remove particulates, and the resultant supernatant fluid was centrifuged at 230,000 g for 1 h. This pellet was then subjected to a series of washes and ultracentrifugations as above. The sample was treated with 10 mM Tris pH 7.4 containing 10% sodium lauryl sulfate and proteinase K (50 μg/ml). After the final ultracentrifugation, the sample was resuspended in 10 mM Tris pH 7.4 (200 μl/g of the initial brain sample).

Hydrophilic Interaction Chromatography (HILIC).

The sample was solubilized in 0.01 M Tris HCl, pH 8.00 containing 2 mM EDTA, 5% SDS and 10% hexafluoro-2-propanol at 100° C. for 10 min. After SDS treatment, the sample was placed in a solvent consisting of 100% acetonitrile containing 0.1% TFA acid and 50 mM hexafluoro-2-propanol (buffer A) and applied to a hydrophilic interaction column. All columns that were used were from PolyLC, Inc. (Columbia, Md., USA) with the dimensions 200×4.6-mm; 5 μm; 300-Å. Three packings were evaluated, PolyWAX LP™ (an anion-exchange material), PolyHYDROXYETHYL A™ (a neutral material) and PolySULFOETHYL A™ (a strong cation-exchange material) (all three trademarks are the property of PolyLC, Inc.). The flow rate was 0.5 ml/min. The conditions for eluting $PrP^{SC}$ were 100% A for 8 min and then a linear gradient to 100% water containing 0.1% trifluoroacetic acid and 50 mM hexafluoro-2-propanol (buffer B) in 15 min, then 100% B for 10 min. Peak fractions were collected and dried in a vacuum centrifuge (Savant Instruments, Inc, Farmingdale, N.Y., USA). Fractions were resuspended in 10 μl of deionized $H_2O$ and the fraction that tested positive by immunoblot for $PrP^{SC}$ was used in a capillary electrophoresis assay.

Labeling Prion Protein With $^{125}I$.

$PrP^{SC}$ was labeled with $^{125}I$ using IODOGEN™ (Pierce, Rockford, Ill., USA). The labeled protein was separated from the free $^{125}I$ by passing it through a solid phase extraction cartridge containing PolyWAX LP™(PolyLC, Inc.) that had been equilibrated with buffer A. The labeled $PrP^{SC}$ was eluted from the cartridge using buffer B. The unbound $^{125}I$ was retained on the cartridge, which could be discarded as solid radioactive waste. The fractions containing the labeled $PrP^{SC}$ were dried in a vacuum centrifuge, dissolved in water, diluted 1/10 in buffer A, and loaded onto the HPLC column.

Dot Blots.

One-μl aliquots of peak fractions from HILIC chromatography were applied to nitrocellulose paper, dried, and then incubated in 20 mM Tris, pH 7.5, containing 500 mM NaCl, 0.05% Tween 20 (TTBS) and 5% fish gelatin for 1 h. The blot was washed 2× with TTBS and then incubated with a dilution of 1/500 of antibodies made to peptides of the prion protein for 3 h at 25° C. (rabbit antibodies to peptide 142–154). After incubation, the blot was washed 2× with TTBS and then incubated with biotinylated protein G (Bio-Rad Laboratories, Hercules, Calif., USA) for 1 h. Again the blot was washed as above. Horseradish peroxidase coupled to NeutrAvidin™ (Pierce, Rockford, Ill., USA) was added to the blot and incubated for 1 h at 25° C. After incubation, the blot was washed 6× with TTBS. After washing, the blot was incubated in the SuperSignal® Substrate(Pierce) system for 10 min and then exposed to Kodak X-OMAT AR (Eastman Kodak Company, Rochester, N.Y., USA) X-ray film for 15 sec.

Binding Assay for $^{125}IPrP^{SC}$.

Fractions containing $^{125}I$ from the PolyWAX LP column were assayed for binding activity to an antibody that had been produced to the peptide corresponding to residues 142–154 of the prion protein. The tubes containing radioactivity were dried in a Savant vacuum centrifuge at 42° C. and resuspended in 10 μl of $H_2O$ and then diluted with buffer-containing salts in 0.1% BSA. A PVC plate was coated with the antibody in 0.1 M $Na_2CO_3$, pH 9.0. After washing with the above buffer, 100 μl of $^{125}I$-$PrP^{SC}$ was incubated on the plates at 37° C. for 2 h and then overnight at 4° C. The plate was washed and cut into individual wells and counted. Background cpm were subtracted from the cpm in the wells.

Capillary Electrophoresis Conditions.

Free zone capillary electrophoresis (Schmerr and Jenny, Electrophoresis 19:409, 1998) was performed on a Beckman P/ACE 5500 (Beckman Instruments, Fullerton, Calif., USA). Laser-induced fluorescence (LIF) detection was done using an air-cooled argon laser (Beckman Instruments) with excitation at 488 nm and emission at 520 nm. Unmodified capillaries were obtained from Beckman Instruments. A 20 cm (length to the detector)×201 μm I.D. capillary was used with 200 mM Tricine, pH 8.0. This buffer contained 0.1% N-octylglucoside (Boehringer Mannheim GmbH, Indianapolis, Ind., USA) and 0.1% BSA (Sigma Chemical Co., St. Louis, Mo., USA). In preparation for the separation, the capillary was rinsed for 1 min with 0.25 M NaOH, rinsed for 2 min with $H_2O$, and then rinsed 2 min with buffer. The separating conditions were 30 KV for 3 min at 20° C. The current was about 20 μA. The sample was injected for 15 sec followed by a 5 sec injection of running buffer. The sample volume was about 0.95 nl. Rinses were carried out under high pressure and sample injection carried out under low pressure.

Immune Complex and Prion Binding Assays.

Fifteen microliters of fluorescein-labeled peptide containing about 2 pmoles of the fluorescent labeled peptide was mixed with affinity-purified rabbit IgG to demonstrate binding of antibody to the fluorescein-labeled peptide. One μl of peak fractions from the HILIC chromatography was added to the assay. After mixing the components, the samples were incubated at 25° C. for the 10 min.

Results.

Figure 1:
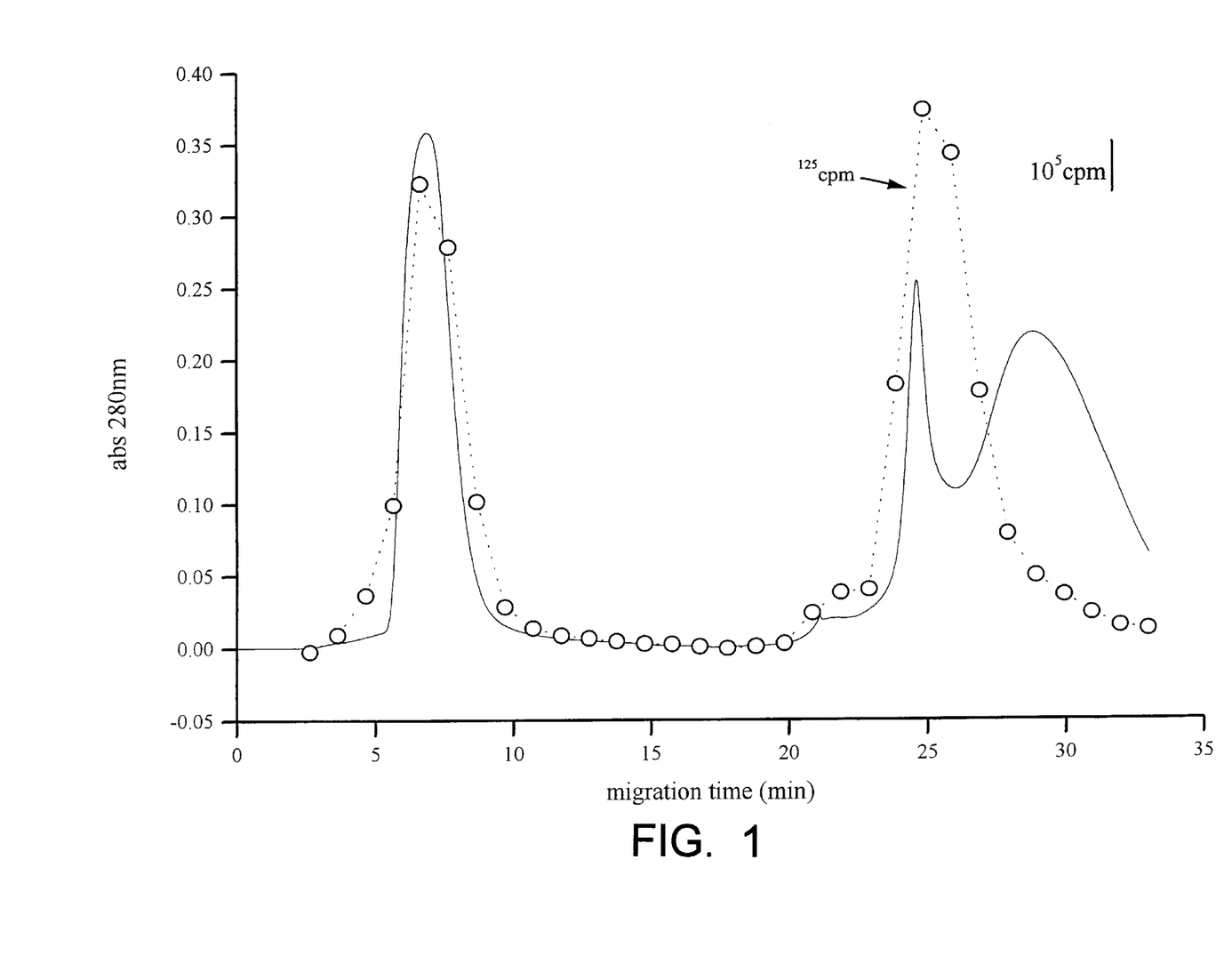
Figure 2:
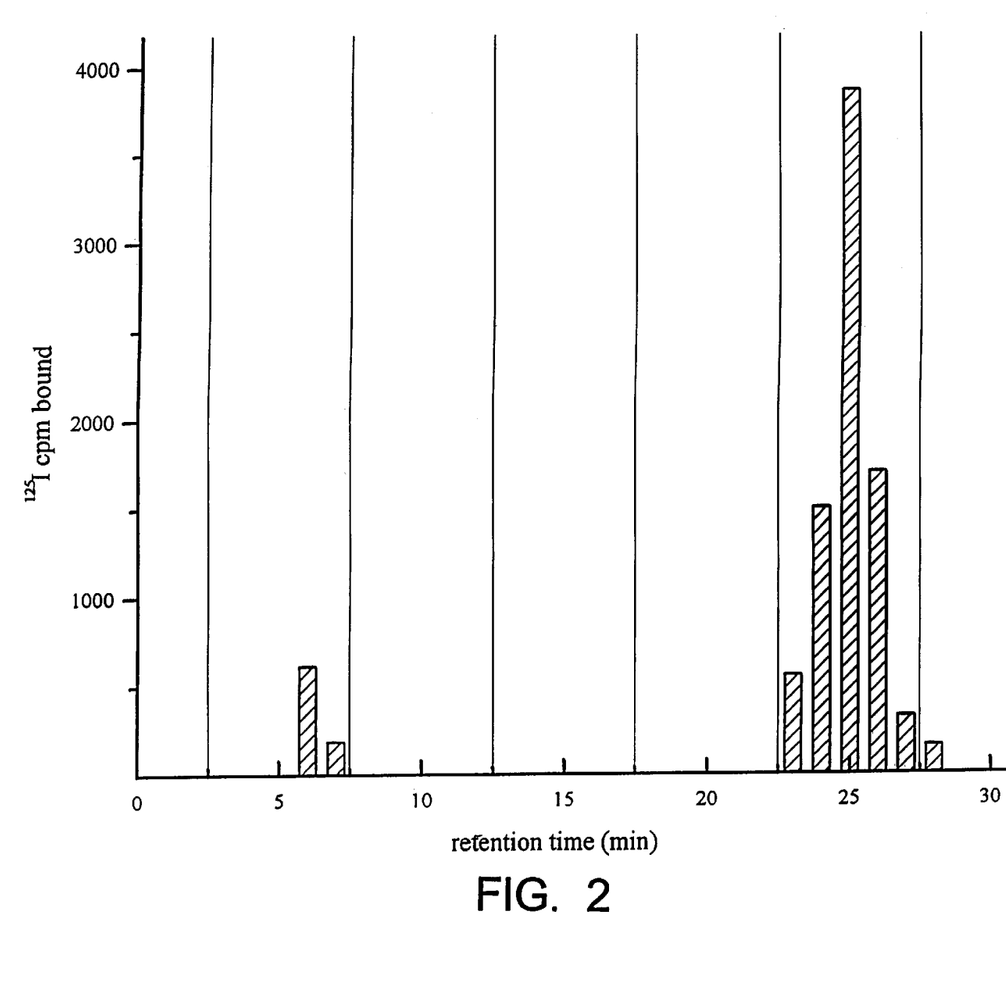

The chromatogram of $PrP^{SC}$ after purification and iodination is shown in FIG. 1. Radioactivity (cpm) from the $^{125}I$-labeled prion protein coincides with the absorbance at 280 nm, except for the last peak detected by absorbance. The yield of abnormal protein, based on recovery of $^{125}I$ cpm loaded onto the column, was about 76%. The peaks of cpm and A280 absorbance coincide with the peaks showing antibody activity in the binding assay (FIG. 2). The main peak in the binding assay at about 25 min coincides with peaks for $^{125}I$-PrP and A280 absorbance at 25 min in FIG. 1. Similar results were obtained for a chromatogram (not shown) from an extraction (unpurified) of scrapie infected sheep brains.

A wide range of pI values have been reported in the literature (Schmerr and Jenny, supra; Safar et al., Proc. Natl. Acad. Sci. USA 87:6373, 1990; Somerville et al., J. Gen. Virol. 70:25, 1989) for abnormal prion protein. The pI of this protein would affect the binding of this protein to column packings. There was no great difference between the retention times on the positively-charged PolyWAX LP column and the neutral PolyHYDROXYETHYL A column. This suggested that the protein might be acidic. Abnormal prion protein samples containing SDS eluted from the negatively-charged PolySULFOETHYL A column in a broad envelope. Accordingly, the abnormal prion protein purified on the PolyWAX LP column was re-run on the PolySULFOETHYL A column. Its elution in or near the void volume indicates that it is indeed acidic. This was confirmed by both gel isoelectric focusing and capillary electric focusing (Schmerr et al., Chromatogr. A. 802:135, 1998). pI values ranged from 3–6 with a major species at 3.00. These results suggest that in hydrophilic interaction chromatography, it is necessary to use a neutral or an anion exchange material.

In capillary immunoelectrophoresis using HILIC purified samples, resultant electropherograms (not shown) indicate that samples from infected sheep did react, whereas samples from normal (noninfected) sheep did not react. Since SDS inhibits typical immunoassays including capillary electrophoresis assays, it is necessary to remove SDS in order to perform such assays. A competition assay using capillary electrophoresis could be performed on samples after HILIC chromatography, since SDS elutes in or near the void volume (Jenö et al., Anal. Biochem., 215:292, 1993).

EXAMPLE 4

Analysis of Abnormal Prion Protein Extracted From Infected Sheep Blood.

Buffy coat centrifuge fractions from blood samples from TSE-infected sheep were diluted with Tris buffered saline (10% tissue:90% buffer). The samples were then treated with proteinase K to digest the normal host prion protein but not the altered abnormal form of prion protein. After digestion, the treated sample was mixed with an equal volume of hexafluoro-2-propanol (HFIP) and incubated at 56° C. for five minutes. An equal volume of 0.5 M sodium sulfate was added and the phases were allowed to separate. The layer containing HFIP was removed and the sample dried in a vacuum centrifuge.

The pellet was resuspended in water and the suspension was put in an organic chromatography mobile phase containing 95% acetonitrile, 5% water, 0.1% trifluoroacetic acid and 50 mM HFIP. The mobile phase was applied to a solid phase extraction cartridge of PolyHYDROXYETHYL Aspartamide™ (PolyLC, Inc.). Abnormal prion protein was eluted from this support with 100% water, 0.1% trifluoroacetic acid and 50 mM HFIP, and then dried and resuspended in water.

The presence of abnormal prion protein was detected by capillary immunoelectrophoresis. Abnormal prion protein was not detected in electropherograms for control samples of blood that was not infected with TSE.

EXAMPLE 5

Analysis of Abnormal Prion Protein Extracted From Infected Mule Deer Blood.

The procedure of Example 4 was repeated with blood samples from TSE-infected mule deer. The presence of abnormal prion protein was detected by capillary immunoelectrophoresis. Abnormal prion protein was not detected in electropherograms for control samples of blood that was not infected with TSE.

EXAMPLE 6

Analysis of Abnormal Prion Protein Extracted From Infected Elk Blood.

The procedure of Example 4 was repeated with blood samples from TSE-infected elk. The presence of abnormal prion protein was detected by capillary immunoelectrophoresis. Abnormal prion protein was not detected in electropherograms for control samples of blood that was not infected with TSE.

All patents, patent applications, test protocols, and publications cited herein are hereby incorporated by reference in their entireties.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. A method for extracting abnormal prion protein from a biological material suspected of containing abnormal prion protein, said method comprising:

(a) incubating a mixture of an extraction solvent and an isotonic or hypotonic aqueous preparation of biological material under conditions effective to extract abnormal prion protein from said biological material into said extraction solvent, wherein said extraction solvent is;
   (i) a polar organic solvent in which said abnormal prion protein is soluble, and
   (ii) miscible with a non-lyotropic aqueous solution but immiscible with a lyotropic aqueous solution; and (b) increasing lyotropic activity of the mixture to separate said extraction solvent from said aqueous preparation of said biological material to yield extraction solvent containing any abnormal prion protein from said biological material.

2. The method as defined in claim 1, wherein said extraction solvent is hexafluoro-2-propanol.

3. The method as defined in claim 1, wherein said biological material is a tissue or a biological fluid from a vertebrate.

4. The method as defined in claim 3, wherein said tissue is brain tissue.

5. The method as defined in claim 3, wherein said biological fluid is selected from the group consisting of cerebrospinal fluid, blood, plasma, and serum.

6. The method as defined in claim 3, wherein said biological fluid is human blood.

7. The method as defined in claim 1, wherein said mixture is incubated at a temperature ranging from about 20° C. to about 100° C.

8. The method as defined in claim 7, wherein said incubation is at about 56° C.

9. The method as defined in claim 1, wherein said lyotropic activity is increased by adding about a 1:1 ratio (vol/vol) of 0.5 M sodium sulfate to said mixture.

10. The method as defined in claim 1, wherein said biological material in said isotonic or hypotonic aqueous preparation of biological material is treated with proteinase K.

11. The method as defined in claim 1, further comprising (c) drying the extraction solvent containing abnormal prion protein to yield an extractant pellet.

12. The method as defined in claim 11, further comprising (d) dissolving said dried extractant pellet in water and purifying said abnormal prion protein.

13. The method as defined in claim 12, wherein said purifying comprises a method selected from the group consisting of hydrophilic interaction chromatography and capillary electrophoresis.

14. A method for detecting the presence of abnormal prion protein in an animal, said method comprising assaying said separated extraction solvent prepared by a method as defined in claim 1 for abnormal prion protein.

15. The method as defined in claim 14 wherein said assay comprises an immunoassay for abnormal prion protein.

16. The method according to claim 14, wherein the biological sample is a tissue or a biological fluid from a vertebrate.

17. The method according to claim 16, wherein said tissue is brain tissue.

18. The method according to claim 16, wherein said biological fluid is selected from the group consisting of cerebrospinal fluid, blood, plasma, and serum.

19. The method as defined in claim 16, wherein said biological fluid is human blood.

20. A method for extracting abnormal prion protein from a biological material suspected of containing abnormal prion protein, said method comprising:

(a) incubating a mixture of about equal amounts of hexafluoro-2-propanol and a non-lyotropic aqueous preparation of biological material under conditions effective to extract abnormal prion protein from said biological material into said hexafluoro-2-propanol;

(b) adding about an equal volume of a solution of 0.5M sodium sulfate to said mixture to separate said hexafluoro-2-propanol from said aqueous preparation of said biological material to yield extraction solvent containing any abnormal prion protein from said biological material.

21. A kit for isolating abnormal prion protein from a biological sample, said kit comprising:

(a) an extraction solvent, wherein the extraction solvent is
  (i) a polar organic solvent in which abnormal prion protein is soluble, and
  (ii) miscible with a hypotonic or isotonic aqueous solution but immiscible with a lyotropic aqueous solution; and (b) a lyotropic salt or aqueous lyotropic salt solution to add to an aqueous preparation of a biological sample so that said organic solvent becomes immiscible with said aqueous preparation.

22. The kit according to claim 21, further comprising a sample container with a volume indicator for said aqueous preparation of a biological sample, wherein said polar organic solvent and said lyotropic salt or aqueous lyotropic salt solution are provided in pre-measured units for use with said sample container.

23. The kit of claim 21, further comprising proteinase-K for treating said aqueous preparation of a biological sample.

24. A kit for detecting the presence of abnormal prion protein from a biological sample, said kit comprising (a) an extraction solvent which is
  (i) a polar organic solvent in which abnormal prion protein is soluble, and
  (ii) miscible with a non-lyotropic aqueous solution but immiscible with a lyotropic aqueous solution;

(b) a lyotropic salt or aqueous lyotropic salt solution to add to an aqueous preparation of a biological sample so that said extraction solvent becomes immiscible with said aqueous preparation; and (c) an abnormal prion protein detection assay.

25. The kit according to claim 24, wherein said detection assay is an immunoassay.

26. The kit according to claim 25, wherein said immunoassay is an immunochromatographic assay.

* * * * *